United States Patent [19]

Madsen et al.

[11] 4,061,757

[45] Dec. 6, 1977

[54] COMPOUNDS HAVING JUVENILE HORMONE ACTIVITY

[75] Inventors: Hans Berg Madsen, Bovlingbjerg; Preben Lindholm Holst; Houk Solli, both of Harboor, all of Denmark

[73] Assignee: A/S Cheminova, Lemvig, Denmark

[21] Appl. No.: 615,960

[22] Filed: Sept. 23, 1975

Related U.S. Application Data

[63] Continuation-in-part of Ser. No. 435,057, Jan. 15, 1974, abandoned, which is a continuation-in-part of Ser. No. 292,375, Sept. 26, 1972, abandoned.

[30] Foreign Application Priority Data

Sept. 27, 1971 United Kingdom ............... 44884/71
Jan. 24, 1973 Denmark ............................ 386/73

[51] Int. Cl.$^2$ .................... C07D 213/30; A61K 31/44
[52] U.S. Cl. ................................. 424/263; 260/297 R; 260/296 R; 542/405; 542/413; 542/424
[58] Field of Search ................... 260/240 R, 297 R; 424/263

[56] References Cited

U.S. PATENT DOCUMENTS

| | | | |
|---|---|---|---|
| 2,500,131 | 3/1950 | Linsker et al. | 260/279 |
| 2,518,130 | 8/1950 | Evans et al. | 260/250 |
| 3,563,982 | 2/1971 | Bowers | 260/240 |
| 3,701,759 | 10/1972 | Lee et al. | 260/240 H |
| 3,838,159 | 9/1974 | Johnston | 260/296 R |
| 3,864,334 | 2/1975 | Pallos | 260/240 H |
| 3,941,777 | 3/1976 | Madsen et al. | 260/240 H |

OTHER PUBLICATIONS

Solli et al., Pestic Sci, vol. 7, pp. 503–511.
Culvenor, Reviews of Pure & Applied Chemistry, vol. 3, pp. 83–114 (1953).

*Primary Examiner*—John M. Ford
*Attorney, Agent, or Firm*—Beveridge, DeGrandi, Kline & Lunsford

[57] ABSTRACT

This invention is concerned with certain substituted 3-hydroxy- or 3-aminopyridines and their preparation and use. These compounds possess improved juvenile hormonal activity which can be utilized first and foremost to inhibit the metamorphosis of insect larvae and, consequently, can be utilized in the control of insects.

32 Claims, No Drawings

COMPOUNDS HAVING JUVENILE HORMONE ACTIVITY

This application is a continuation-in-part of our earlier copending U.S. patent application Ser. No. 435,057, filed Jan. 15, 1974, now abandoned, which in turn is a continuation-in-part of our U.S. patent application Ser. No. 292,375, filed Sept. 26, 1972, but now abandoned.

This invention is for improvements in or relating to chemical compounds having juvenile hormone activity. More particularly, the present invention relates to methods and compositions for the control of insects, to novel terpenoid ethers and amines of 3-pyridinols and 3-amino pyridines.

A number of substances are known which have juvenile hormone activity demonstrated by retention of larval characters, inhibition of metamorphosis and stimulation of ovarian growth in adult females. For a comprehensive review see: Slama, K., Annual Review of Biochemistry, 40, 1079, (1971).

It is known from the patent literature that terpenoid aromatic ethers and amines show juvenile hormone activity: Belgian Pat. No. 734,904, West German Pat. OLS No. 2,000,113 and Schwartz, M. et al. Journ. Econ. Ent. 63, 1858, (1970).

Some compounds of this type exhibit high activity when applied topically to the insect, stimulate its development and prevent formation of sexually mature adults. Compounds exhibiting this activity may be envisaged as potential insecticides of the third generation.

The compounds of the present invention act selectively on certain insects and, moreover, exhibit high sterilizing properties. The compounds, the preparation and application of which is described herein, represent analogs of the insect juvenile hormone with higher activity for some insects than known analogs.

The compounds of the present invention are represented by the following general formula I:

in which A and B, when taken together, represent a further single bond between the adjacent carbon atoms, or an oxygen bridge, or, when taken individually, A represents a hydrogen atom, and B represents a lower alkyl group, a lower alkoxy group or a hydroxy group, C and D, when taken together, represent a further single bond between the adjacent carbon atoms, or, when taken individually, C and D each represent a hydrogen atom, R and $R_1$ each represent a methyl or ethyl group, $R_2$ represents a hydrogen atom or at least one substituent, selected among halogen atoms, lower alkyl, lower alkoxy and nitro groups, and X is O or NH. $R_2$ can be a substituent in any position on the pyridine nucleus, preferably in the 2'-position, but more preferably in the 6'-position, or in the 2'- and 6'-positions, when there are two substituents.

For the present purpose, the compounds with a double bond in the 2-position may be designated as "geranyl compounds". The compounds without any double bond in the 2-position may be designated as "citronellyl compounds".

The term "lower alkyl", as used herein, refers to a straight or branched chain saturated aliphatic hydrocarbon group having a chain length of one to six carbon atoms, such as methyl, ethyl, propyl, i-propyl, t-butyl, pentyl and n-hexyl. The lower alkyl in the lower alkoxy group has the same significance. The terms "alkyl" and "alkoxy" also include alkyl and alkoxy containing simple substituents, such as hydroxy or halogen. As halogen atoms, chlorine and bromine atoms are preferred.

Preferred compounds of the present invention are compounds of formula I in which A and B, when taken together, represent a further single bond or an oxygen bridge, or, when taken individually, A represents a hydrogen atom and B represents a methyl, ethyl, methoxy or ethoxy group, C and D have the above meaning, X is an oxygen atom, R and $R_1$ each represent a methyl or ethyl group, and $R_2$ is a hydrogen atom or an alkyl or alkoxy group having 1–3 carbon atoms, or compounds of formula I in which A and B, when taken together, represent a further single bond or an oxygen bridge, or, when taken individually, A represents a hydrogen atom and B represents a methyl, ethyl, methoxy or ethoxy group, C and D have the above meaning, X is NH, R and $R_1$ each represent a methyl or ethyl group, and $R_2$ is a hydrogen atom or an alkyl or alkoxy group having 1–3 carbon atoms, or compounds of formula I in which A and B, when taken together, represent a further single bond or an oxygen bridge, or, when taken individually, A represents a hydrogen atom and B an alkyl or alkoxy group having 1–2 carbon atoms, C and D have the above meaning, R and $R_1$ each represent an alkyl group having 1-2 carbon atoms, and $R_2$ is an alkyl group having 1-2 carbon atoms.

The compounds of the general formula I are prepared by a process in which a. a compound of the general formula II

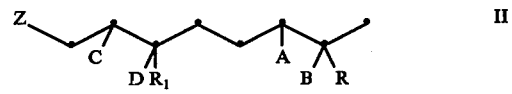

wherein A, B, C, D, R and $R_1$ have the meaning stated above, and AB preferably represent a single bond, and Z is Cl, Br or I, is reacted with a compound of one of the formulae III and IV

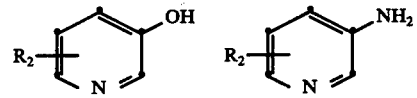 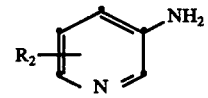

wherein $R_2$ has the meaning stated above, or b. a compound of the general formula I, wherein A and B, taken together, represent a single bond between the adjacent carbon atoms, is reacted with an epoxidizing agent, to form a compound of formula I wherein A and B represent, taken together, an oxygen bridge, or c. a compound of formula II, wherein A and B, taken together, represent a single bond between the adjacent carbon atoms, is reacted with an epoxidizing agent to form a compound of formula II, wherein A and B, taken together, represent an oxygen bridge, whereupon the latter compound is reacted with a compound of one of the formulae III or IV to form the corresponding compound of formula I, or d. a compound of the general formula I, wherein A and B, taken together, represent a single bond between the adjacent carbon atoms, is reacted (1) with a mercuric salt in an appropriate alcohol or (2) with a mercuric salt in a mixture of water and tetrahydrofuran, whereupon the resulting oxymercuric intermediate product is reduced to form a compound of formula I, wherein A is hydrogen, and B is (in case (1)) lower alkoxy or (in case (2)) hydroxy, or e. compound of formula II, wherein A and B, taken together, represent a single bond, is reacted (1) with a mercuric salt in an appropriate alcohol (2) with a mercuric salt in a mixture of water and tetrahydrofuran, and the resulting oxymercuric intermediate product is reduced to form a compound of formula II, wherein A is hydrogen, and B is (in case (1)) lower alkoxy, or (in case (2)) hydroxy, whereupon the latter compound is reacted with a compound of one of the formulae III or IV to form the corresponding compound of formula I.

The reaction (a) between a compound of formula II and a compound of formula III is preferably performed in the presence of an acid neutralizing substance in an organic solvent, especially potassium hydroxide in dimethylformamide.

The ethers of formula I, wherein X is O, can be prepared according to (a) from the chloride or bromide of the compound of formula II by reaction with a 10% molar excess of the appropriate 3'-pyridinol and powdered KOH in dimethyl-formamide or a 1,2-dimethoxyethane/ethanol mixture (1:1 by volume).

The reaction mixture is stirred for 3-20 hours at temperatures between 20° and 60° C, diluted with water and extracted with ether or n-hexane. The organic extracts are washed with 10% KOH solution and finally with water, then dried over anhydrous $Na_2SO_4$. The solvent is removed in vacuo, and the resulting crude ether is purified by column chromatography on Silica Gel. The crude ether is dissolved in a benzene/ethylacetate mixture (4:1 by volume) and applied on the column, and then eluted with a benzene/ethylacetate mixture, starting with 4:1. During the elution the concentration of ethylacetate is gradually increased.

The purity can be established to 99+% by GLC and combined spectrometric methods.

The reaction (a) between a compound of formula II and a compound of formula IV is preferably performed in an organic solvent, especially dimethylsulfoxide.

The N,3-substituted 3'-aminopyridines of formula I wherein X is NH, can be prepared according to (a) from the chloride or bromide of the compound of formula II by reaction with equimolar amounts of the appropriate 3'-aminopyridine in dimethylsulfoxide. The reaction mixture is stirred for 3-5 hours at room temperature, 0.1 N NaOH is added, extracted with ether, washed with water and dried over anhydrous $Na_2SO_4$. The solvent is removed in vacuo, and the resulting crude amine is purified as described above. The purity can be established to 99+% by combined chromatographic and spectrometric methods.

The epoxidation according to (b) or (c) is preferably performed with m-chloroperbenzoic acid.

The epoxidation according to (b) gives usually better results than the epoxidation according to (c).

The compounds of formula I can be epoxidized according to (b) by reaction with m-chloroperbenzoic acid in methylenechloride at 0°-5° C for 2 hours. A 10% molar excess of peracid is used and the epoxidation takes place selectively at the terminal 6-7 position. The reaction mixture is poured into an ice-cold 10% aqueous $NaHCO_3$ solution and shaken thoroughly, washed with water, dried over $Na_2SO_4$ and evaporated in vacuo. The epoxide is purified by column chromatography as described above. The purity can usually be more than 99%.

The reduction according to (d) or (e) is preferably performed by means of $NaBH_4$ in aqueous sodium hydroxide.

The terminally substituted compounds of the general formula I, wherein B represents a lower alkoxy group and A a hydrogen atom, can be prepared according to (d) or (e) by the oxymercuration procedure of Brown and Geoghegan (J.A.C.S., 91. 5646, (1969)). The compounds of formula (I) or (II) are treated with mercuric acetate in the appropriate alcohol and the resulting oxymercuric intermediate is reduced by adding aqueous 3 M NaOH and 0.5 M $NaBH_4$ in 3 M NaOH. The mixture is allowed to stir for 2 hours, until the mercury has coagulated and settled. The product is extracted with n-hexane, washed with water, dried over $Na_2SO_4$ and the solvent is removed in vacuo. The alkoxylated halogenides of formula II are reacted with pyridinols of formula III or with aminopyridines of formula IV according to the procedures described above, to form the terminally alkoxylated compounds of general formula I. The crude products are purified by column chromatography as described above. According to chromatographic and NMR analysis, the alkoxylated products consist principally of the terminal (C-7) derivatives. The purity can usually be more than 99%.

The starting materials, compounds with the general formula II, can be either geranyl- or citronellylbromide or -chloride or 1-bromo-3-ethyl-7-methyl-6-nonena, or 1-bromo-3-ethyl-7-methyl-2,6-nonadiene. The latter may be prepared by the Marc Julia synthesis (Bull. Soc. Chem. France 1072, (1960)) according to the scheme below:

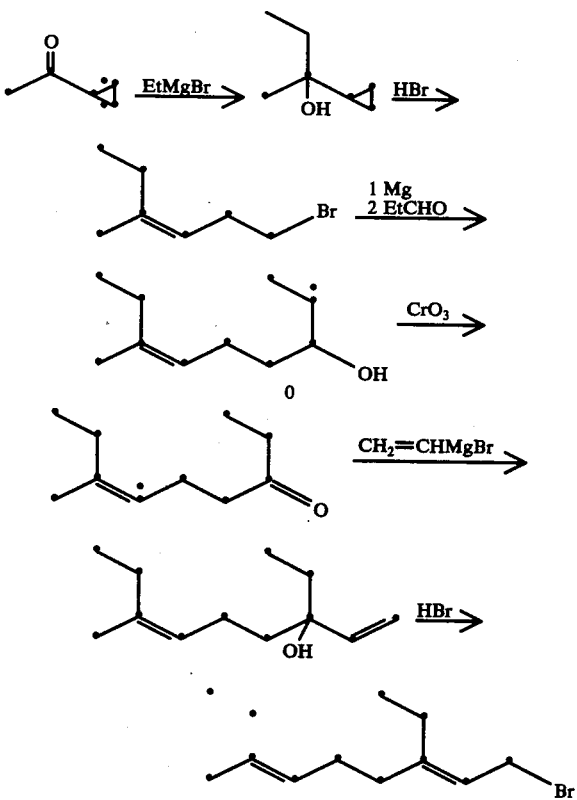

All chemical structures are confirmed by a combination of IR and NMR data.

In accordance with the present invention, there is provided a method for the control of insects, which comprises contacting the insects with a compound selected from those of formula I in an amount effective to inhibit the metamorphosis of said insect or to act as sterilizing or ovicidal agent.

Said compounds have been found to act on species of different orders all over the class of insects, viz. Coleoptera (beetles, weevils), Lepidoptera (butterflies, moths), Hemiptera (bugs, plant lice, scales), Orthoptera (grass hoppers), Dictyoptera (roaches), and Diptera (mosquitoes, flies).

Accordingly, the invention includes a composition containing a compound of the formula I and a suitable carrier, which composition is suitable for the control of insect pests. To achieve a uniform distribution or application, it is advantageous to employ a composition comprising an inert carrier and, as the essential active ingredient, a compound of formula I.

One method for the control of insects in accordance with the present invention is to apply the composition comprising an inert carrier and a compound of formula I to the locus of insect infestation, such as to the plant life on which insects live. These composition can be either solid or liquid.

Solid compositions for treating insects can be prepared by incorporating the active ingredient with an inert carrier such as finely divided talc, silica pyrophyllite, diatomite or clay or granular inert carriers, such as the vermiculites.

Liquid compositions can be prepared by mixing the active compound with inert carriers, such as acetone, xylene, peanut oil, cotton-seed oil, sesame oil and other vegetable oils and mineral oils conventionally employed as carriers in insecticidal formulation for application by spraying. Emulsions containing the active ingredient can also be used.

Other ingredients can be present in the composition of the present invention to aid in the effective application of the active ingredient, such as wetting agents, dispersing agents, insect attractants and the like.

The concentration of active ingredient of a compound of formula I in the composition can vary depending on a variety of factors, such as the specific insect involved, the degree of insect infestation, the locus of insect infestation, environment and weather conditions, and type of application device used.

Generally, the composition will contain less than 95% by weight of the active ingredient and more frequently less than 10% by weight.

The compounds of formula I are useful insect control agents by virtue of their ability to inhibit the metamorphosis of said insect. The expression "to inhibit the metamorphosis of said insect" as used herein, and in the appended claims, is used to describe the direct insecticidal effect of the compounds of formula I as well as the indirect insecticidal effects of said compounds.

The compounds of formula I inhibit metamorphosis of various insect species at different stages, resulting in non viable intermediates. Depending on the time of application, the compounds of formula I show ovicidal, larvicidal or pupicidal effect. When applied to the adult insect, the effect is indirect in the sense that the insect produces non viable eggs.

The morphogenetic activity of some of the compounds with the general formula I are given in Table 1.

Quite generally, the compounds with a substituent in the 6'-position are the most active. Furthermore, a terminal epoxy function in the geranyl or citronellyl side chain hances the activity approximately tenfold compared to the corresponding compounds of formula I, wherein A and B, taken together, represent a further single bond. A similar increment in activity is obtained with an ethoxy group in the C-7 position. Substitution with ethyl- instead of methyl- branching in the geranyl or citronellyl side chain also enhances the activity about tenfold.

The compounds of formula I are very potent and thus can be used at extremely low levels, for example $10^{-6}$ to $10^{-9}$ g. and are thus advantageously administered over large areas suitable for the specific insect population. These compounds are superior to classical insecticides as they are broken down at a fairly rate and will cause no accumulation in nature. Furthermore, they show no mammalian toxicity. The acute oral toxicity in mice of the compounds with general formula I is more than 5000 mg/kg.

The invention also includes a pharmaceutical composition containing a compound of the formula I having juvenile hormone activity.

The following examples are presented to illustrate the present invention.

EXAMPLE 1

Ether formation

Preparation of 3,7-dimethyl-1-(6'-methyl-3'-pyridyloxy)-2,6-octadiene. A mixture of 12 g. (0,11 mol) 6-methyl-3-hydroxypyridine and 7 g. powdered KOH (85%) in 100 ml dimethylformamide is stirred for 45 min.. 17.2 g. (0.1 mol) geranylchloride is added and the reaction mixture is stirred overnight at room temperature. 100 ml water is added to the reaction mixture, extracted with n-hexane, washed with 10% aqueous KOH and with water until neutral. The extract is dried over anhydr. $Na_2SO_4$ and the solvent removed in vacuo. Yield: 17.2 g. of crude ether. Purified on a Silica Gel column as described below. The infrared spectrum exhibits the characteristic absorption bands due to the disubstituted pyridine nucleus and bands showing the presence of an ether function and methylene double bonds. NMR: 1.61 ppm and 1.67 ppm (7-$CH_3$), 1.74 ppm (3-$CH_3$), 2.07 ppm and 2.12 ppm (4-$CH_2$ and 5-$CH_2$), 2.48 ppm (6-$CH_3$), 4.56 ppm doublet, 1-$CH_2O$), 5.07 ppm (multiplet, 6-H), 5.45 ppm (triplet, 2-H), doublet centered at 7.08 ppm (4'- and 5'-H), 8.2 ppm (2'-H). $n_D^{24}$ = 1.516

EXAMPLE 2

Epoxidation

Preparation of 6,7-epoxy-3,7-dimethyl-1-(6'-methyl-3'-pyridyloxy)-2-octene. To a stirred, chilled (0° C) solution of 2.5 g. (0.01 mol) 3,7-dimethyl-1-(6'-methyl-3'-pyridyloxy)-2,6-octadiene in 50 ml methylenechloride is cautiously added 2.4 g. (0.011 mol) 85%'s m-chloro-perbenzoic acid dissolved in 30 ml methylenechloride. The reaction mixture is stirred on an icebath for 2 hours, 10% aqueous $NaHCO_3$ solution is added and shaken thoroughly. The aqueous layer is extracted with methylenechloride and the combined extracts evaporated in vacuo. The residue is dissolved in ether, washed twice with 10% $NaHCO_3$ solution and finally twice with water. The etheral extract is dried over anhydr. $Na_2SO_4$ and evaporated in vacuo. The crude product is purified by column chromatography. NMR: Doublet centered at 1.28 ppm (2 × 7-CH$_3$), 1.77 ppm (3-CH$_3$), 1-CH$_2$O), 5.5 ppm (triplet 2-H), doublet centered at 7.1 ppm (4'- and 5'-H), 8.2 ppm (2'-H). n$_D^{24}$ = 1.511.

EXAMPLE 3 a

Ethoxylation

Preparation of 7-ethoxy-3,7-dimethyl-1-(6'-methyl-3'-pyridyloxy)-2-octene. 2.50 g. (0.01 mol) 3,7-dimethyl-1-(6'-methyl-3-pyridyloxy)-2,6-octadiene is added to a vigorously stirred suspension of 3.2 g (0.01 mol) mercuric acetate in 30 ml of 99% ethanol. Ten minutes after the addition of the diene, the mercurial intermediate is reduced by adding 10 ml aqueous 3 M NaOH and 10 ml 0.5 M NaBH$_4$ in 3 M NaOH.

The mixture is allowed to stir for two hours, until the mercury has coagulated and settled. Then the product is extracted with n-hexane, washed with water until neutral, dried over Na$_2$SO$_4$ and the solvent is removed in vacuo. The crude product is purified by column chromatography. NMR: 1.08 ppm (triplet, CH$_3$CH$_2$O-), 1.15 ppm (2 × 7-CH$_3$), 1.75 ppm (3-CH$_3$), 2.48 ppm (6'-CH$_3$), 3.3 ppm (quartet, CH$_3$CH$_2$O-), 5.5. ppm (triplet, 2-H), doublet centered at 7.1 ppm (4'- and 5'-H), 8.2 ppm (2'-H), 4.56 ppm (doublet, 1-CH$_2$O). n$_D^{24}$ = 1.504

EXAMPLE 3 b

Preparation of 7-ethoxy-geranylchloride (1-chloro-7-ethoxy-3,7-dimethyl-2-octene). 3.4 g geranylchloride (0.02 mol) is added to a vigorously stirred suspension of 6.4 g. mercuric acetate in 30 ml of 99% ethanol at 0° C. One hour after the addition of the diene, the mercurial intermediate is reduced by adding 20 ml 3 M NaOH and 20 ml 0.5 M NaBH$_4$ in 3 M NaOH. Then following the procedure described above.

7-Ethoxy-3,7-dimethyl-1-(6'-pyridyloxy)-2-octene is prepared according to the ether formation procedure of Example 1 from 2.2 g 7-ethoxy-geranylchloride, 1.1 g. 6-methyl-3-hydroxypyridine, 1 g. powdered KOH (85%) in 15 ml dimethylformamide

EXAMPLE 3 c

Hydration

Preparation of 7-hydroxy-3,7-dimethyl-1-(6'-methyl-3'-pyridyloxy)-2-octene. In a small flask, fitted with a magnetic stirrer, is placed 3.2 g. (0.01 mol) of mercuric acetate. To this flask is added 10 ml of water, followed by 10 ml of tetrahydrofuran. Then 2.5 g. (0.01 mol) 3,7-dimethyl-1-(6'-methyl-3'-pyridyloxy)-2,6-octadiene is added. The reaction mixture is stirred for ten minutes at room temperature, and the mercurial intermediate is reduced by adding 30 ml aqueous 3 M NaOH and 30 ml 0.5 M NaBH$_4$ in 3 M NaOH. The product is obtained following the procedure described in Example 3a. n$_D^{24}$ = 1.521

EXAMPLE 4

N,3'-Alkylation

Preparation of N,3'-3,7-dimethyl-2,6-octadienyl-1-(3'-a-minopyridine). 1.7 g (0.01 mol) geranylchloride is added to a stirred solution of 1.0 g. (0.011 mol) 3-aminopyridine in 10 ml dimethyl sulfoxide. The reaction mixture is stirred for 4 hours at room temperature. Then 20 ml water is added, made alkaline with 0.1 N NaOH, extracted with ether, washed with water and dried over anhydr. Na$_2$SO$_4$. n$_D^{24}$ 1.508.

EXAMPLE 5

Ether formation

Preparation of 3,7-dimethyl-1-(6'-methyl-3'-pyridyloxy)-6-octene. A mixture of 1.2 g.(0.011 mole) 6-methyl-3-hydroxy-pyridine and 0.7 g. pulverized potassium hydroxide (85%) in 20 ml dimethylformamide is agitated for 30 minutes. 2.6 g.(0.01 mole) citronellyliodide is added, and the reaction mixture is agitated overnight by room temperature. 20 ml water is added, and the total mixture is extracted by means of n-hexane. The extract is washed by means of a 10% aqueous potassium hydroxide and then by means of water until neutral reaction of the wash water. The extract is dried over water-free sodium sulfate, and the solvent is removed in vacuo.

Yield: 1.85 g. of the crude ether stated in the heading, which ether is purified on a Silica Gel column. n$_D^{24}$: 1.490.

EXAMPLE 6

Epoxidation

Preparation of 6,7-epoxy-3,7-dimethyl-1-(6'-methyl-3'pyridyloxy)-octane. To an agitated and cooled (0° C) solution of 1 g.(0.004 mole) 3,7-dimethyl-1-(6'-methyl-3'-pyridyloxy)-6-octene in 50 ml methylenechloride is cautiously added 0.9 g.(0.0044 mole) m-chloroperbenzoic acid (85%). The reaction mixture is agitated in an ice bath for 4 hours. A 10% aqueous solution of sodium hydrogencarbonate is added, and the mixture is vigorously shaken. The aqueous phase is extracted by means of methylenechloride, and the combined extracts are evaporated in vacuo. The evaporation residue is dissolved in ethyl ether, the solution is washed two times by means of a 10% aqueous solution of sodium hydrogencarbonate and then two times by means of water. The ethereal extract is dried over water-free sodium sulfate and is evaporated in vacuo. THe crude product containing the ether stated in the heading is purified by means of column chromatography. n$_D^{24}$: 1.493.

EXAMPLE 7

Ethoxylation and ether formation

Preparation of 7-ethoxy-citronellyliodid (1-iodo-7-ethoxy-3,7-dimethyl-octane). 1.3 g. citronellyliodide (0.005 mole) is added to a vigorously agitated suspension of 1.6 g. mercuric acetate in 10 ml 99% ethanol at 0° C. After 45 minutes 5 ml 3 M aqueous sodium hydroxide solution and then 0.1 g. sodium boronhydride (NaBH$_4$) in 5 ml aqueous 3 M sodium hydroxide solution are added with cooling. The reaction mixture is agitated for 1 hour and left for standing until the mercury has coagulated. Then the product is extracted with n-hexane, washed with water until neutral, and dried over sodium sulfate. The solvent is evaporated in vacuo. The crude product is used directly in the following step of the synthesis.

7-Ethoxy-3,7-dimethyl-1-(6'-methyl-3'-pyridyloxy)-octane is prepared by the ether-formation process described in example 5 from 0.5 g. 7-ethoxy-citronellyliodide, 0.2 g. 6-methyl-3-hydroxypyridine and 0.01 g. potassium hydroxide (85%) in 5 ml dimethylformamide. The reactinon product containing the ether stated in the heading is purified by means of column chromatography. $n_D^{24}$: 1.479.

EXAMPLE 8

Chromatography 9 g. crude 3,7-dimethyl-11-(6'-methyl-3'-pyridyloxy)-2,6-octadiene is fractionated by column chromatography on Silica Gel (0.2 - 0.5 mm). The column is filled with 280 g. Silica Gel and a benzene/ethylacetate mixture (4:1 by volume). The elution is started with a 4:1 mixture of benzene/ethylacetate (200 ml), and then gradually increasing the concentration of ethylacetate during the elution: 3:1 (200 ml), 7:3 (400 ml), 6.5:3.5 (300 ml) and finally 3:2 (200 ml).

Yield: 7.5 g. pure ether. The same procedure was applied to all other compounds

The nuclear magnetic resonance (NMR) was recorded on a Varian Associate 60 MNz spectrometer, with deuterated chloroform as solvent and tetramethylsilane as the internal standard.

In accordance with the example given above, the following compounds may be prepared:

No. 6 — 3,7-Dimethyl-1-(3'-pyridyloxy)-2,6-octadiene.

NMR.: 1,62 and 1,68 ppm (7-CH$_3$), 1,76 ppm (3-CH$_3$), 2,07 and 2,11 ppm (4-CH$_2$ and 5-CH$_2$), 4,51 ppm (doublet, 1-CH$_2$O), 5,07 ppm (multiplet, 6-H), 5,45 ppm (triplet, 2-H), multiplet centered at 7,20 ppm (4'- and 5'-H), multiplet centered at 8,20 ppm (2'- and 6'-H).

No 7 —
3,7-Dimethyl-1-(6'-ethyl-3'-pyridyloxy)-2,6-octadiene.

NMR.: 1,25 ppm (triplet, 6'-CH$_3$CH$_2$), 1.62 and 1,68 ppm (7-CJ$_3$), 1,75 ppm (3-CH$_3$), 2,08 and 2,12 ppm (4-CH$_2$ and 5-CH$_2$), 2,73 ppm (quartet, 6'-CJH$_3$CH$_2$), 4,53 ppm (doublet, 1-CH$_2$O), 5,08 ppm (multiplet, 6-H), 45,46 ppm (triplet, 2-H), 6,98 ppm (multiplet, 4'- and 5'-H) 8,12 ppm (2'-H).

No. 8 —
3,7-Dimethyl-1-(6'-isopropyl-3'-pyridyloxy)-2,6-octadiene.

NMR.: 1,25- ppm (doublet, 6'-(CH$_3$)$_2$CH), 2.94 (septet, 6'-(CH$_3$)$_2$CH).

The other ppm values are analogues with those stated for the geranyl chain in substance No. 7. The same applies for the prtones 2'-, 4'- and 5'-H of the pyridine ring.

No. 9 —
3,7-Dimethyl-1-(6'-methoxy-3'-pyridyloxy)-2,6-acetadiene.

NMR.: 3,86 ppm (6'-OCH$_3$), 7,23 ppm (multiplet, 4'- and 5'-H), multiplet centered at 8,40 ppm (2'-H), The other ppm values are analogues with those stated for the geranyl chain in substance No. 7.

No. 10 — 3-Ethyl-7-methyl-11-(6'-methyl-3'-pyridyloxy)-2,6-nonadiene.

NMR.: 0,98 ppm (triplet, 3- and 7-CH$_3$CH), 1,60 ppm (7-CH$_3$), komplex band between 1,8- and 2,5 - ppm (3-, 4-, 5-, 8-CH$_2$), 2,48 ppm (6'-CH$_3$), 4,55 ppm (doublet, 11-CH$_2$O), 5,10 ppm (6-H, multiplet), 5,47 ppm (triplet, 2l-H), doublet centered at 7,1 ppm (4'-and 5'-H), 8,2 ppm (multiplet, 2'-H).

No. 11 —
3-EThyl-7-methyl-1-(6'-ethyl-3'-pyridyloxy)-2,6-nonadiene.

NMR.: 1,25 ppm (triplet, 6'-CH$_3$CH$_2$), 2,73 ppm (quartet, 6'-CH$_3$CH$_2$), multiplet centered at 6,98 ppm (4'- and 5':H), 8,12 ppm (2'-H). The other values are analogues with those stated for the 3-methy;-7-methyl-2,6-nonadiene-chain in substance No. 10.

No. 12—6,7-Epoxy-3,7-dimethyl-11-(3'-pyridyloxy)-2-ocetene.

NMR.: Doublet centered at 1,28 ppm (2×7-CH$_3$) 1,77 ppm (3-CH$_3$), 2,7 ppm (triplet, 6-H), 4,55 ppm (doublet, 1-CH$_2$O), 5,5 ppm (triplet, 2-H), doublet centered at 7,2 ppm (4'- and 5'-H), multiplet centered at 7,2 ppm (2'- 6'-H).

N. 13 13 6,7-Epoxy-3,7-dimethyl-11-(6'-ethyl-3'-pyridyloxy)-21-octene.

NMR.: Doublet centered at 1,28 ppm (2×7 CH$_3$), 1,25 ppm (triplet, 6'-CH$_3$CH$_2$), 1,77 ppm (3-CH$_3$), 2,7 ppm (triplet, 6-H), 2,73 ppm (quartet, 6'-CH$_3$CH$_2$), 4,55 ppm (doublet, 11-CH$_2$O), 5,5ppm (triplet, 2-H), 7,0 ppm (multiplet, 4'- and 5'-H), 8,12 ppm (2'-H). $n_D^{26} = 1,498$

No. 14 —
6,7-Epoxu-3-ethyl-7-methyl-1-(6'-methyl-3'-pyridyloxy)-2-nonene.

NMR: 0,99 ppm (7-CH$_3$CH$_2$, triplet), 1,2 ppm (7-CH$_3$), komplex band between 1,8 and 2,4ppm (3- and 4-CH$_2$), 2,48 ppm (6'-CH$_3$), 2,6 ppm (triplet, 6-H), 5,45 ppm (triplet, 2-H), doublet centered at 7,1 ppm (4'- and 5'-H) 8,2 ppm (multiplet, 2'-H).

No. 15 — 6,7 Epoxy-3-ethyl-7-methyl-1-(6'-ethyl-3'-pyridyloxy)-21-nonene.

NMR.: 1,25 ppm (triplet, 6'-CH$_3$CH$_2$), 2,73 ppm (quartet, 6'-CH$_3$CH$_2$), 7,0 ppm (multiplet, 4'- and 5'-H), 8,12 ppm (multiplet, 2'-H). The other ppm-values are analogues with those stated for the 6,7-epoxy-3-ethyl-7-methyl-2-nonene-chain in substance No. 14.

No. 16 —
7-Ethoxy-3,7-dimethyl-1-(3'-pyridyloxy)-2-octene.

NMR.: 1,08 ppm (triplet, CH$_3$CH$_2$O-), 1,15 ppm (2×7-CH$_3$), 1,75 ppm (3-CH$_3$), 3,3 ppm (quartet, CH$_3$CH$_2$ O-) 5,5ppm (triplet, 2-H), 4,56 ppm (doublet, 1-CH$_2$O), doublet centered at 7,2 ppm (4'- and 5'-H), multiplet centered at 8,2 ppm (2'- and 6'-H).

No. 17 — N, 3'-3,7-Dimethyl-2,6-octadienlyl-(6'methoxy-3'-aminopyridin).

NMR.: 1,62 and 1,68 ppm (2×7 -CH$_3$), 1,72 ppm (3-CH$_3$), komplex band between 2,05 and 2,12 ppm (4- and 5-CH$_2$), 3,48 ppm (doublet, 1-CH$_2$), 3,86 ppm )6'-OCH$_3$), 4,68 ppm (N-H), komplex bands at 5,1 and 5,5 ppm (2- and 6-H), multiplet centered at 7,25 ppm (4'- and 5'-H), 8,4 ppm (2'-H).

Furthermore, the following compounds were prepared by using similar procedures as stated in the Examples:

No. 18 — 3-Ethyl-7-methyl-1-(3'-pyridyloxy)-2,6-nonadiene; $n_D^{24} = 1.526$

No. 10 — 6,7-Epoxy-3-ethyl-7-methyl-1-(3'-pyridyloxy)-2-nonene; $n_D^{24} = 1.521$ No. 20 — 7-Methoxy-3,7-dimethyl-11 -(3'-pyridyloxy)-2-ocetene;$n_D^{24}$ = 1.498

No. 21 — 7-Metoxy-3,7-dimethyl-1-(6'-methyl-3'-pyridyloxy)-2-octene;

No. 22 —7-Ethoxy-3-ethyl-7-methyl-1-(3'-pyridyloxy)-2-nonene; $N_D^{24}$ = 1.512 No. 23 — 7-Ethoxy-3-ethyl-7-methyl-11 -(6'-methyl-3'-pyridyloxy)-2-nonene; $n_D^{24}$ = 1.508

No. 24 — 3,7-Dimethyl-11 -(2'-nitro-6'-methyl-3'-pyridyloxy)-2,6-octadiene; $n_D^{24}$ = 1.556

No. 25 — 3,7-Dimethyl-1-(2'-hydroxymethyl-3'-pyridyloxy)-2,6-octadiene; $n_D^{24}$ = 1.541.

No. 26 — 3,7 Dimethyl-1-(2'-methyl-3'-pyridyloxy)-2,6-octadiene; $n_D^{24}$ = 1.497

No. 27 — 7-Ethoxy-3,7-dimethyl-1-(6'-ethyl-3'-pyridyloxy)-2-octene; $n_D^{26}$ = 1.505

No. 28 — 7-Methoxy-3,7-dimethyl-1-(6'-ethyl-3'-pyridyloxy)-2-octene; $n_D^{26}$ = 1,501

No. 29 — 3,7-Dimethyl-1-(6'-ethyl-3'-pyridyloxy)-2,6-nonadiene; $n_D^{26}$ = 1.507

No. 30 — 6,7-Epoxy-3,7-dimethyl-11 -(6'-ethyl-3'-pyridyloxy)-21 -nonene; $n_D^{26}$ = 1.510

No. 31 — 3,7-Dimethyl-1-(2'-hydroxymethyl-6'-methyl-3'pyridyloxy)-2,6-octadiene; $n_D^{26}$ =1.530

No. 3,7-Dimethyl-1-(3'-pyridyloxy)-6-octene; $n_D^{24}$ = 1.491

No. 33 — N,3'-3,7-Dimethyl-6-Octenyl-11 -(3'-aminopyridine)

N. 37 — 3,7-Dimethyl-1-(6'-ethyl-3'-pyridyloxy)-6-octene; $n_D^{26}$ = 1.494

No. 38 — 6,7-Epoxu-3,7-dimethyl-11 -(6'-ethyl-3'-pyridyloxy)-octane; $n_D^{26}$ = 1.493

No. 39 — 7-Ethoxy-3,7-dimethyl-11 -(96'-ethyl-3'-pyridyloxy)-octane; $n_D^{26}$ = 1.483

No. 40 — 7-Methoxy-3,7-dimethyl-11 -(6'-ethyl-3'-pyridyloxy)-octane; $n_D^{26}$ = 1.489

No. 41 — 7-Ethoxy-3,7-dimethyl-1-(6'-ethyl-3'-pyridyloxy)-2-nonene.

NMR.: 1,25 ppm (triplet, 6-CH$_3$CH), 2,73 ppm (quartet, 6'-CH$_3$CH$_2$) 7,0 ppm (multiplet, 4'- and 5'-H), 8,12 ppm (multiplet, 2'-H). The other ppm-vaues are analogues with those stated for the 7-ethoxy-3,7-dimethyl-2-octene-chain in substance No. 16.

EXAMPLE 9

Formulation

The active ingredient prepared according to Example 1 — or any of the other active ingredients mentioned above — can be formulated in the followyg way:

| Active ingredient | 10.0 grammes |
|---|---|
| 70% Ca-dodecylphenylsulfonate | 5.0 grammes |
| Oleyl-poly(15)ethyleneoxideether | 5.0 grammes |
| Acetone | ad 100 millilitres |
| | (100 g/l a.i.) |

When poured into water, an emulsion is immediately formed, which shortly after is transformed into a true solution. Further dilution into any desired concentration can be performed.

The water based solution is ready for spraying.

Testing of juvenile hormone activity

The biological tests are examplified by tests on the yellow mealworm, *Tenebrio molitor L, Galleria mellonella L, Culex pipiens L, Aedes aegypti L* and *Drosophila melanogaster L.*

Tenebrio test: The material in question is applied topically to the abdomen of 0.5 to 2 hours old pupae of the said species, as a solution in acetone. The pupae are held at 27° C and 70% RH, ecdysis occuring 5 to 7 days later. The degree of inhibition of adult characters is referred to an arbitrary scale, where a morphologically perfect adult is given the character 0%, and a perfect second pupae 100%. In Table 1 is given the morphological inhibition dose 50% (ID 50 morph.) for some of the chemicals invented, in μg per standard pupa (150 mg). ID 50 morph. refers to specimens showing predominantly adult characters in the front part, pupal characters in the abdomen.

Galleria test: The test is performed on eggs deposited on impregnated filter paper by the mother moth. The data given in table 2, are the amount necessary for preventing eclosion of 50% of the eggs. The amount IC-50 eclos.) is given in mg./65 cm$^2$.

Culex test: The compounds are tested on mature larvae. The concentration necessary to produce a loss of 50% of the test animals is given in table 2. The concentration (IC-50 eclos.) is given in ppm.

Aedes test: The same test as for Culex.

Drosophila test: One ml of acetone solution of the compound to be tested is mixed with an artificial agar based food mixture just before this solidifies. Ten less than one day old adult flies — five of each sex — are added, and all abnormalities observed for two generations. Juvenile hormone activity is especially noted in the pupae which fail in ecdysis. EC$_{50}$-eclos. is given in ppm.

In the following table I, the compounds Nos. 1–5 are the compounds prepared in the Examples 1, 2, 3a, 3c and 4, while the compounds Nos. 34–36 are the compounds prepared in the Examples 5, 6 and 7. The remaining compounds are those indicated by numbers above.

Table I

| Compound No. | Tenebrio test ID-50 morph. μg/pupa | Galleria test IC-50-eclos. mg/65 cm$^2$ | Culex test IC-50 eclos. ppm | Drosophila test EC-50 eclos ppm | Aedes test IC-50 eclos ppm |
|---|---|---|---|---|---|
| 1 | 0.02 | 0.2 | 0.5 | > 100 | 0.5 |
| 2 | 0.002 | — | — | — | 0.1 |
| 3 | 0.001 | — | < 10 | — | — |
| 4 | 4.0 | — | — | — | — |
| 5 | 40.0 | — | 10 | — | — |
| 6 | 3.0 | — | — | — | — |
| 7 | 0.005 | < 10 | 0.05 | > 100 | — |
| 8 | 0.004 | — | — | — | — |
| 9 | 0.02 | — | — | — | — |
| 10 | 0.002 | — | — | — | — |
| 11 | 0.001 | — | — | — | — |
| 12 | 0.2 | — | — | — | — |

Table I-continued

| Compound No. | Tenebrio test ID-50 morph. μg/pupa | Galleria test IC-50-eclos. mg/65 cm² | Culex test IC-50 eclos. ppm | Drosophila test EC-50 eclos ppm | Aedes test IC-50 eclos ppm |
|---|---|---|---|---|---|
| 13 | 0.0001 | 0.2 | 0.005 | > 100 | 0.1 |
| 14 | 0.002 | — | — | — | — |
| 15 | 0.0001 | — | — | — | — |
| 16 | 0.009 | — | — | — | — |
| 17 | 0.4 | — | — | — | — |
| 18 | 0.2 | — | — | — | — |
| 19 | 0.02 | — | — | — | — |
| 20 | 1.0 | — | — | — | — |
| 21 | 1.0 | — | < 10 | — | 1 |
| 22 | 0.01 | — | — | — | — |
| 23 | 0.001 | 0.005 | 0.5 | — | — |
| 24 | 75. | — | > 10 | — | — |
| 25 | 10. | — | — | — | — |
| 26 | 10. | — | — | — | — |
| 27 | 0.0001 | 0.2 | < 1 | > 100 | — |
| 28 | 0.001 | — | — | — | — |
| 29 | 0.02 | 0.5 | — | > 100 | — |
| 30 | 0.0003 | 1. | < 10 | > 100 | 0.5 |
| 31 | 10 | 20. | > 10 | — | — |
| 32 | 5. | 10. | 0.2 | — | — |
| 34 | 0.4 | 1. | 0.5 | — | — |
| 35 | 0.05 | — | — | — | — |
| 36 | 0.05 | — | — | > 100 | — |
| 37 | 0.2 | 1. | — | > 100 | — |
| 38 | 0.005 | > 10 | < 10 | > 100 | < 1 |
| 39 | 0.01 | 10 | < 10 | > 100 | 0.5 |
| 40 | 0.02 | < 1 | — | > 100 | — |

The advantageous activity of the compounds of the invention compared with known aromatic terpene ethers having juvenile hormone activity (using Tenebrio tests) can be seen from the following table.

Table II

Known compounds.

| R | n | ED$_{50}$ (μg/pupa) |
|---|---|---|
| CH$_3$ | 0 | 1,0 |
| C$_2$H$_5$ | 0 | 0,1 |
| i-C$_3$H$_7$ | 0 | 0,8 |
| CH$_3$O | 0 | 1,5 |
| CH$_3$ | 1 | 0,05 |

Compounds of the formula I

| X | R | R$_1$ | B | A | R$_2$ | ID$_{50}$ morph. (μg/150 mg pupa) |
|---|---|---|---|---|---|---|
| O | CH$_3$ | CH$_3$ | bond | | 6'-CH$_3$ | 0,02 |
| O | CH$_3$ | CH$_3$ | bond | | 6'-C$_2$H$_5$ | 0,005 |
| O | CH$_3$ | CH$_3$ | bond | | 6'-i-C$_3$H$_7$ | 0,004 |
| O | CH$_3$ | CH$_3$ | bond | | 6'-CH$_3$O | 0,02 |
| O | CH$_3$ | CH$_3$ | -O- | | 6'-CH$_3$ | 0,002 |

Data for the known compounds are given in Nature, Vol. 232, Aug. 13, 1971 (page 486-487).

ED$_{50}$ is the effective dose causing abnormal development of 50% of the treated pupae.

ID$_{50}$morph is as said above the dose causing development of individuals showing predominantly adult characters in the front part and pupal characters in the abdomen. It is known that ID$_{50}$-doses in general are 10 times greater than ED$_{50}$-doses.

It is seen from table II that the compounds of the invention are superior to known compounds. This superiority appears even more clearly when the said difference between ID$_{50}$-doses and ED$_{50}$-doses is taken into consideration.

What is claimed is:

1. A chemical compound corresponding to the formula

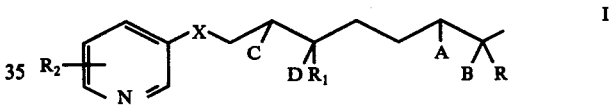

in which A and B, when taken together, represent a further single bond between the adjacent carbon atoms, or an oxygen bridge, or, when taken individually, A represents a hydrogen atom, and B represents a lower alkyl group, a lower alkoxy group or a hydroxy group, C and D, when taken together, represent a further single bond, or, when taken individually C and D each represent a hydrogen atom, R and R$_1$ each represent a methyl or ethyl group, R$_2$ represents a hydrogen atom or at least one substituent selected from the group consisting of halogen atoms, lower alkyl, lower alkoxy and nitro groups, and X is 0.

2. A compound as claimed in claim 1, in which R$_2$ in formula I means a single substituent in the 6'-position.

3. A compound as claimed in claim 2, in which A and B, when taken together, represent a further single bond or an oxygen bridge, or, when taken individually, A represents a hydrogen atom and B represents a methyl, ethyl, methoxy or ethoxy group R and R$_1$ each represent a methyl or ethyl group, and R$_2$ is a hydrogen atom or an alkyl or alkoxy group having 1-3 carbon atoms.

4. A compound as claimed in claim 2, in which A and B, when taken together, represent a further single bond or an oxygen bridge, or, when taken individually, A represents a hydrogen atom and B an alkyl or alkoxy group having 1-2 carbon atoms, R and R$_1$ each represent an alkyl group having 1-2 carbon atoms, and R$_2$ is an alkyl group having 1-2 carbon atoms.

5. A composition for the control of insects which comprises an inert carrier and a compound as claimed in claim 1, the composition containing said compound in an amount effective to inhibit the metamorphosis of insects.

6. A composition as claimed in claim 5, wherein the inert carrier is a liquid in the form of a spray.

7. A composition according to claim 8, which contains 7-ethoxy-3,7-dimethyl-1-(6'-ethyl-3'-pyridyloxy)-2-octene.

8. A composition according to claim 5, which contains 6,7-epoxy-3,7-dimethyl-1-(6'-ethyl-3'-pyridyloxy)-2-nonene.

9. A composition according to claim 5 which contains 3,7-dimethyl-1-(3'-pyridyloxy)-2,6-octadiene.

10. A composition according to claim 5 which contains 3,7-dimethyl-1-(6'-methyl-3'-pyridyloxy)-2,6-octadiene.

11. A composition according to claim 5 which contains 3,7-dimethyl-1-(6'-propyl-3'-pyridyloxy)-2,6-octadiene.

12. A composition according to claim 5 which contains 3,7-dimethyl-1-(6'-methoxy-3'-pyridyloxy)-2,6-octadiene.

13. A composition according to claim 5 which contains 3-ethyl-7-methyl-1-(3'-pyridyloxy)-2,6-nonadiene.

14. A composition according to claim 5 which contains 3-ethyl-7-methyl-1-(6'-methyl-3'-pyridyloxy)-2,6-nonadiene.

15. A composition according to claim 5 which contains 6,7-epoxy-3,7-dimethyl-1-(3'-pyridyloxy)-2-octene.

16. A composition according to claim 5 which contains 6,7-epoxy-3,7-dimethyl-1-(6'-methyl-3'-pyridyloxy)-2-octene.

17. A composition according to claim 5 which contains 6,7-epoxy-3-ethyl-7-methyl-1-(3'-pyridyloxy)-2-nonene.

18. A composition according to claim 5 which contains 6,7-epoxy-3-ethyl-7-methyl-1-(6'-methyl-3'-pyridyloxy)-2-nonene.

19. A composition according to claim 5 which contains 7-methoxy-3,7-dimethyl-1-(3'-pyridyloxy)-2-octene.

20. A composition according to claim 5 which contains 7-methoxy-3,7-dimethyl-1-(6'-methyl-3'-pyridyloxy)-2-octene.

21. A composition according to claim 5 which contains 7-ethoxy-3,7-dimethyl-1-(3'-pyridyloxy)-2-octene.

22. A composition according to claim 5 which contains 7-ethoxy-3,7-dimethyl-1-(6'-methyl-3'-pyridyloxy)-2-octene.

23. A composition according to claim 5 which contains 7-ethoxy-3-ethyl-7-methyl-1-(3'-pyridyloxy)-2-nonene.

24. A composition according to claim 5 which contains 7-ethoxy-3-ethyl-7-methyl-1(6'-methyl-3'-pyridyloxy)-2-nonene.

25. A composition according to claim 5 which contains 3,7-dimethyl-1-(3'-pyridyloxy)-6-octene.

26. A composition according to claim 5 which contains 3,7-dimethyl-1-(6'-methyl-3'-pyridyloxy)-6-octene.

27. A composition according to claim 5 which contains 7-ethoxy-3,7-dimethyl-1-(6'-methyl-3'-pyridyloxy)-octane.

28. A composition according to claim 5 which contains 6,7-epoxy-3,7-dimethyl-1-(6'-methyl-3'-pyridyloxy)-octane.

29. A composition according to claim 5 which contains 6,7-epoxy-3,7-dimethyl-1-(6'-ethyl-3'-pyridyloxy)-octane.

30. A composition for the control of insects which comprises an inert carrier and a compound as claimed in claim 2, the composition containing said compound in an amount effective to inhibit the metamorphosis of insects.

31. A composition for the control of insects which comprises an inert carrier and a compound as claimed in claim 3, the composition containing said compound in an amount effective to inhibit the metamorphosis of insects.

32. A composition for the control of insects which comprises an inert carrier and a compound as claimed in claim 4, the composition containing said compound in an amount effective to inhibit the metamorphosis of insects.

* * * * *